United States Patent [19]

Sjostrom

[11] Patent Number: 5,133,729

[45] Date of Patent: Jul. 28, 1992

[54] MOTOR DRIVEN HAND PIECE FOR A SURGICAL TOOL

[75] Inventor: Douglas D. Sjostrom, Wakefield, Mass.

[73] Assignee: Smith & Nephew Dyonics Inc., Andover, Mass.

[21] Appl. No.: 569,082

[22] Filed: Aug. 17, 1990

[51] Int. Cl.⁵ .............................................. A61B 17/32
[52] U.S. Cl. ................................... 606/180; 604/22; 408/124
[58] Field of Search .................. 604/22; 606/167–168, 606/170–171, 180; 408/124, 127, 199, 226

[56] References Cited

U.S. PATENT DOCUMENTS

| | | |
|---|---|---|
| 3,409,213 | 11/1968 | Latham . |
| 3,519,201 | 7/1970 | Eisel et al. .................. 223/21 |
| 3,990,453 | 11/1976 | Douvas et al. . |
| 4,167,943 | 9/1979 | Banko ........................ 128/305 |
| 4,167,944 | 9/1979 | Banko ........................ 128/305 |
| 4,203,444 | 5/1980 | Bonnell et al. ............... 128/276 |
| 4,246,902 | 1/1981 | Martinez ..................... 128/305 |
| 4,517,977 | 5/1985 | Frost ......................... 128/305 |
| 4,623,028 | 11/1986 | Murdoch et al. . |
| 4,649,919 | 3/1987 | Thimsem et al. .............. 128/305 |
| 4,705,038 | 11/1987 | Sjostrom .................... 606/180 |
| 4,895,146 | 1/1990 | Draenert .................. 606/180 X |
| 4,951,690 | 8/1990 | Baker ....................... 128/898 |

FOREIGN PATENT DOCUMENTS 0189807 8/1986 European Pat. Off. .
0190000 8/1986 European Pat. Off. .

Primary Examiner—C. Fred Rosenbaum
Assistant Examiner—Corrine Maglione
Attorney, Agent, or Firm—Fish & Richardson

[57] ABSTRACT

A surgical device including a handpiece adapted to receive a surgical tool, a motor driven drive shaft for rotating the tool about an axis, a static seal element sealed to the motor assembly, and a dynamic seal element sealed to the drive shaft, the seal elements having mating sealing portions defining a face seal in a surface transverse to the axis of rotation of the drive shaft.

19 Claims, 4 Drawing Sheets

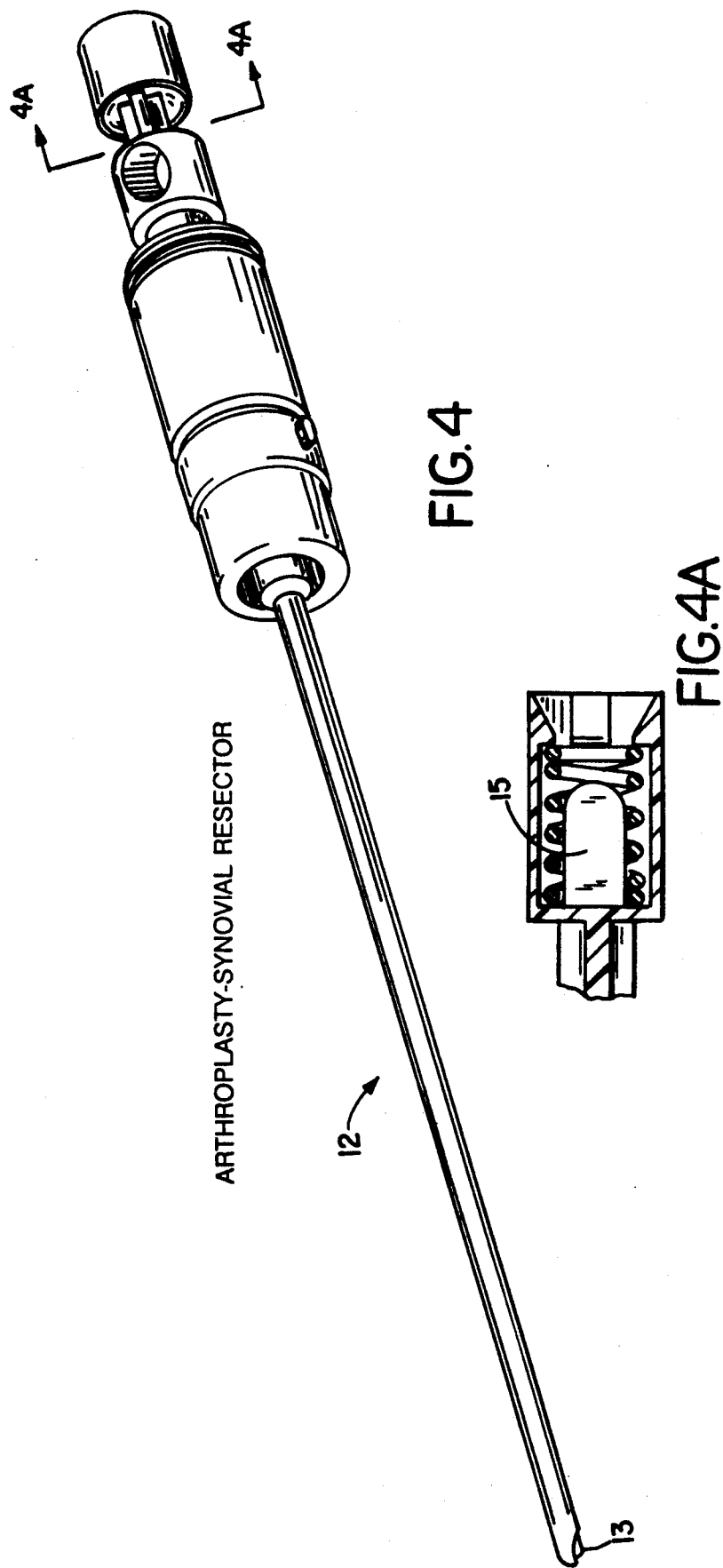

MOTOR DRIVEN HAND PIECE FOR A SURGICAL TOOL

BACKGROUND OF THE INVENTION

The invention relates to surgical devices having motor driven handpieces which receive rotatable surgical tools.

Surgical devices, e.g., for arthroscopic surgery, typically include a handpiece containing a motor and having a distal portion adapted to receive a surgical tool, e.g., an arthroplasty resector. In such systems, the distal tip of the surgical tool usually defines a vacuum passage through which fluid and tissue are removed from a patient's body during surgery. The passage extends from the distal tip of the surgical tool through the tool and into a drain tube in the handpiece which is connected to a suction device. Sometimes, however, the fluid and tissue also enter the motor through the space created between the motor housing and the rotating drive shaft, causing the motor to malfunction and corrode.

One known solution to this problem is to provide flexible lip seals or O-rings around the drive shaft which contact the surface of the drive shaft and seal it parallel to its axis of rotation. The O-rings and the lips of the lip seals, i.e., those portions of the seals which contact the drive shaft, are very flexible, e.g., formed of silicone rubber, or formed of a cover material and some type of filler such as Teflon ® and a graphite compound. In addition, systems which use the O-ring and lip sealing techniques are also known to use close tolerance fitting of the bearings with the drive shaft to prevent the surgical device from rotating off center and pulling away from a portion of the seal, thereby allowing fluids to enter the motor housing.

SUMMARY OF THE INVENTION

In general, the invention features a handpiece adapted to receive a surgical tool, a motor driven drive shaft for rotating the tool about an axis, a static seal element sealed to the motor assembly, and a dynamic seal element sealed to the drive shaft, the seal elements having mating sealing portions defining a face seal in a surface transverse to the axis of rotation of the drive shaft.

Preferred embodiments have the following features. The face seal is in a planar surface perpendicular to the axis of rotation. The dynamic seal element is biased against the static seal element by circumferentially spaced springs that act through an axially movable drive ring and a resilient buffer ring. Surrounding the drive shaft, the drive ring is rotatably keyed to the shaft and the dynamic seal element. An O-ring surrounds the drive shaft, provides a seal between the shaft and the dynamic seal element, and maintains a distance between the shaft and the dynamic seal element. The static seal element is sealed to the handpiece housing by a pair of silicone O-rings, to prevent fluid from flowing past the motor assembly. Finally, the dynamic seal element and the static seal are flat lapped within three helium light bands.

The advantages of the present invention include preventing fluid from entering the motor by providing the face seal transverse to the axis of rotation, particularly in situations where a fluid passageway from the surgical tool exposes the motor housing to fluid. In addition, the face seal is maintained regardless of whether the drive shaft wobbles, and motor vibrations in the handpiece are reduced. The seals between the dynamic seal element and the drive shaft, and between the static seal element and the handpiece housing, further protect the motor.

Other advantages and features will become apparent from the following description, and from the claims.

DESCRIPTION OF THE PREFERRED EMBODIMENT

FIG. 4 is a perspective view of a rotatable surgical tool used with the surgical device shown in FIG. 1 and connectable to the drive shaft shown in FIGS. 2 and 3.

FIG. 4a is an enlarged perspective view, partially cut away and in cross section, of the detail area of FIG. 4.

Figure 1:
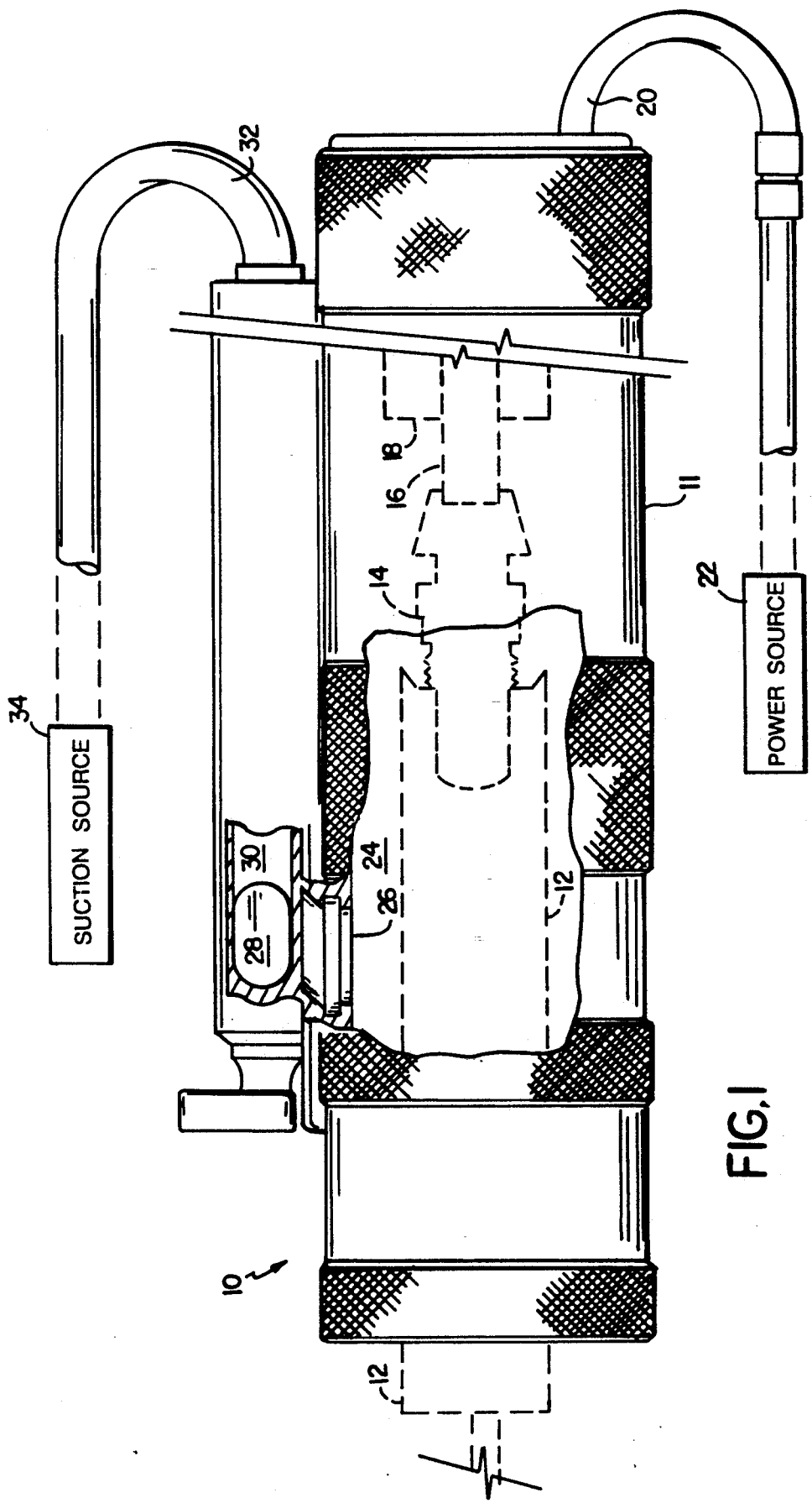
FIG. 1 is a plan view, partially cut away and in cross section, of a surgical device according to the present invention.

Referring to FIG. 1, a surgical device according to the present invention includes a cylindrical surgical handpiece 10, having an outer housing 11, the length and diameter of which are sized and textured to fit comfortably into the palm of a surgeon. The distal end of the handpiece 10 is adapted to receive a rotatable surgical tool 12 (shown in dotted lines in FIG. 1), e.g., an arthroplasty resector (shown in FIG. 4). The tool 12 engages a rotatable drive shaft 14 (shown in dotted lines in FIG. 1) which is bonded, e.g. by Loctite 620 adhesive, to a rotatable motor shaft 16 extending distally from a conventional electric motor 18 (the motor shaft and the motor also shown in dotted lines in FIG. 1) into a recess in the drive shaft 14. This bonding causes the drive shaft 14 to rotate with the motor shaft 16 relative to the handpiece 10, in turn rotating the tool 12.

Extending from the proximal end of the handpiece 10, a power line 20 connects the motor 18 to a power source 22 or other control device to regulate the action of the tool 12, e.g., its rotation speed. Referring to FIG. 4, the distal end of the tool 12 defines an opening 13 which communicates with proximal portions of the tool. Thus, as shown in FIG. 1, when the tool 12 is connected to the drive shaft 14, e.g, by a flange 15 (shown in detail in FIG. 4a) engaged in the distal end of the drive shaft, fluid can flow from a patient's body through the tool and collect in a passageway 24 exposed to the drive shaft and motor housing.

Referring again to FIG. 1, the passageway 24 is defined by the open areas between the tool 12 and the inner wall of the handpiece 10, and between the drive shaft 14 and the inner wall of the handpiece. Most of the fluid exits the passageway 24 through a port 26 and a rotary valve 28 into a channel 30 connected to a drain tube 32. Fluid in the channel 30 is then suctioned through the drain tube 32 by a suction source 34 connected to the tube. Nevertheless, it is possible for some fluid to remain within the passageway 24, which presents a potential hazard should the fluid seep into the motor 18 and cause it to malfunction or corrode. As described below in connection with FIGS. 2 and 3, the present invention provides an improved sealing assembly to prevent fluid from reaching the motor 18.

Figure 2:
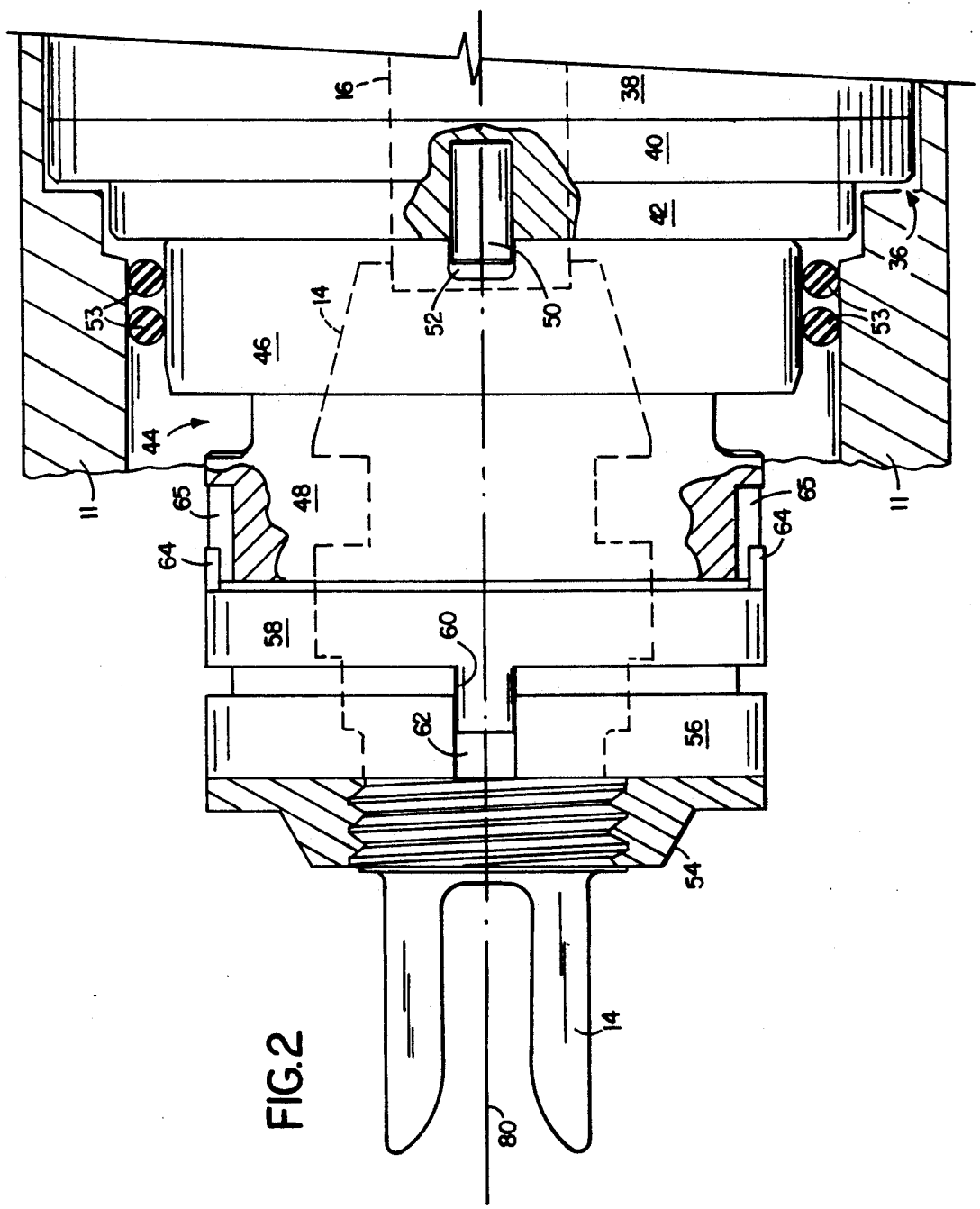
FIG. 2 is an enlarged plan view, partially cut away and in cross section, of a portion of the handpiece shown in FIG. 1, including the drive shaft and the motor housing.
Figure 3:
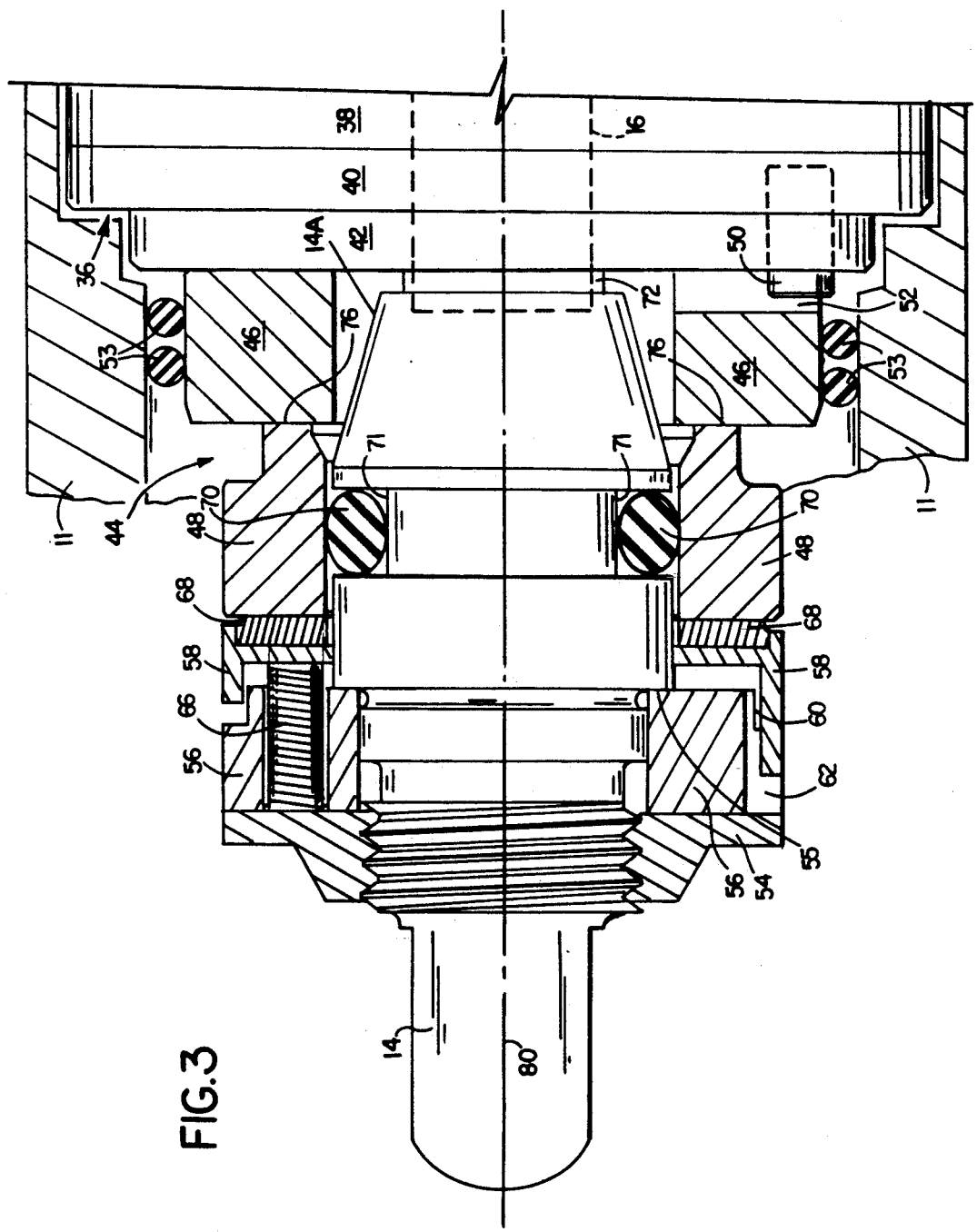
FIG. 3 is a plan view of the portion of the handpiece shown in FIG. 2, but rotated approximately 90° and further cut away and in cross section to show additional detail.

Referring to FIGS. 2 and 3, the handpiece 10 further contains a motor housing 36 which includes a ring gear section 38, a ball bearing section 40, and a shoulder section 42, which are pressed and swaged together to form a 3-piece assembly. Adjacent to the distal end of the motor housing 36 and surrounding the proximal end of the drive shaft 14 is a seal assembly 44 which includes a static seal ring 46 and a dynamic seal ring 48. The static ring 46 is rotationally fixed relative to the motor housing 36 by a pin 50 that extends from within the motor housing and fits into a slot 52 cut into the proximal face of the static ring. The static ring 46 is not otherwise attached to the motor housing 36, but rather is held in place against the motor housing by the adjacent dynamic ring 48 which rotates with the drive shaft 14.

Referring in particular to FIG. 2, a pair of silicone O-rings 53 seal between the static ring 46 and the main housing 11 of the handpiece, to prevent fluid from flowing past the motor assembly. In order that the dynamic ring 48 may rotate with the drive shaft 14, a cap ring 54 is screwed over a threaded portion of the distal U-shaped end of the drive shaft 14, thereby causing the cap ring to rotate with the drive shaft. Adjacent to the cap ring 54 is a spring ring 56 captured between the cap ring 54 and shoulder 55 of shaft 14 so as to rotate with the shaft. Next, a drive ring 58 is rotatably connected to the spring ring 56 by a tab 60 on the drive ring which fits into a slot 62 cut into the spring ring. Thus, the drive ring rotates with the drive shaft 14. And finally, the dynamic ring 48 is rotatably connected to the drive ring 58 by a pair of tabs 64 (180° apart), which fit into slots 65 in the dynamic ring.

Referring to FIG. 3, in order to hold the dynamic ring 48 and the static ring 46 together and create a seal, a number of springs 66 (nine in total, each approximately 0.25 inches in length, 0.057 inches in diameter, and formed of ¼ free length 0.008 inch wire) are circumferentially spaced around the drive shaft 14 in holes drilled through the spring ring 56. The springs 66 act against the cap ring 56 and press the drive ring 58, which is axially movable along the drive shaft 14, toward the dynamic ring 48. Disposed around the drive shaft 14, between the drive ring 58 and the dynamic ring 48, is a buffer ring 68, which is preferably formed of silicone rubber. The buffer ring 68 acts as a resilient interface between the drive ring and the dynamic ring to insulate seal rings 46 and 48 from vibrations during operation of the device, and to avoid direct contact between the metal drive ring 58 and the distal surface of the dynamic ring 48, all to increase the operating life of the seal.

Referring still to FIG. 3, the dynamic ring 48 surrounding the drive shaft 14 is sealed thereto by an O-ring 70 disposed in a groove 71 formed in the drive shaft, thus closing a secondary fluid leakage path to the motor and maintaining a constant distance between the drive shaft 14 and the dynamic ring 48 should the drive shaft 14 begin to wobble, thereby helping to preserve the seal formed between the mating portions of the dynamic ring 48 and the static ring 46. Immediately adjacent to the O-ring, is a tapered proximal end portion 14a of the drive shaft 14. The tapered portion 14a is bonded as described above to the distal end of the motor shaft 16 (shown in dotted lines), thereby causing the drive shaft 14, and all components described above as being rotatably connected thereto, to rotate with the motor shaft 16 relative to the handpiece 10. In addition, surrounding the motor shaft 16, is a washer 72 which acts as a spacer between the tapered portion 14a and the motor housing 36.

More specifically, the mating portions of the static ring 46 and the dynamic ring 48 form a face seal 76 in a plane perpendicular to the drive shaft axis 80. Generally, the face seal 76 is formed toward the inner edge of the static ring 46 because the proximal portion of the dynamic ring 48, i.e., that portion which makes contact with the static ring 46, is stepped inwardly on the surface of its outer diameter so that the mating portion of the dynamic ring is approximately ⅓ the width of the mating portion of the static ring 46. Although the face seal 76 generally remains at the inner edge of the static ring 46, it can sometimes shift towards an outer edge of the static ring because of a lack of rigidity or a side to side wobble in the drive shaft 14. Nevertheless, the shape of the dynamic ring 48 and its positioning relative to the static ring 46 allow the drive shaft 14 to wobble relative to the motor housing 36 without disturbing the face seal 76, i.e., the mating portion of the dynamic ring simply slides radially along the mating portion of the static ring.

The dynamic and static rings 48 and 46 are preferably formed of silicon carbide and a carbon graphite composite, respectively. Also, in order to provide as effective a face seal as possible, the contacting faces of the dynamic and static rings 48 and 46 are polished to a very flat surface free of scratches and grooves, e.g., flat lapped within two or three helium light bands. The solid materials chosen are preferred over the more flexible materials used in previous sealing arrangements, e.g., Teflon and silicone rubber, because they are not sensitive to the material or finish of the drive shaft. Previously used materials were prone to wear out quickly, in part because they contacted the drive shaft itself, a disadvantage that the placement of the rings in the present invention avoids. Finally, the harder materials used in the present invention are resistant to abrasives and other contaminants in the environment, thus ensuring a greater lifetime of use for the motor 18.

In sum, the surgical device of the present invention provides several advantages over previously known surgical devices using O-ring or lip seal arrangements. Most notably, an effective face seal is achieved transverse of the axis of rotation of the drive shaft, and the seal is maintained regardless of whether the drive shaft wobbles. In addition, the materials of the sealing elements are not prone to warp or wear out quickly, nor are they likely to become contaminated. And finally, vibrations in the handpiece are reduced.

Other embodiments are within the following claims.

What I claim:

1. A surgical device for operating a rotatable surgical tool, said surgical device comprising:
   a handpiece adapted to receive said surgical tool;
   a drive shaft for engaging said surgical tool;
   a motor assembly for rotating said drive shaft about an axis;
   a static seal element sealed to said motor assembly to remain stationary with respect to said rotating drive shaft;
   a dynamic seal element sealed to said drive shaft so that said dynamic seal element rotates with said drive shaft;

said stationary static seal element and said rotating dynamic seal element having mating sealing portions defining a face seal in a surface transverse to said axis of rotation of said drive shaft.

2. The surgical device of claim 1 further comprising a passageway communicating with said surgical tool to receive fluids flowing from a patient's body during surgery, said drive shaft and said motor assembly being exposed to said passageway, said face seal preventing fluid from flowing from said passageway into said motor assembly.

3. The surgical device of claim 2 further comprising:
a port defined through a wall of said handpiece;
a channel adjacent to said handpiece having an opening corresponding to said port; and
a suction means for removing at least some of the fluids from said passageway through said port and said channel.

4. The surgical device of claim 1 wherein said surface is planar.

5. The surgical device of claim 4 wherein said planar surface is perpendicular to said axis.

6. The surgical device of claim 1 wherein said static seal element and said dynamic seal element are rings, the outer diameter of said static seal element being greater than the outer diameter of said dynamic seal element.

7. A surgical device for operating a rotatable surgical tool, said surgical device comprising:
a handpiece adapted to receive said surgical tool;
a drive shaft for engaging said surgical tool;
a motor assembly for rotating said drive shaft about an axis;
a static seal element sealed to said motor assembly to remain stationary with respect to said rotating drive shaft;
a dynamic seal element sealed to said drive shaft so that said dynamic seal element rotates with said drive shaft;
said stationary static seal element and said rotating dynamic seal element having mating sealing portions defining a face seal in a surface transverse to said axis of rotation of said drive shaft; and
a passageway communicating with said surgical tool to receive fluids flowing from a patient's body during surgery, said drive shaft and said motor assembly being exposed to said passageway, said face seal preventing fluid from flowing from said passageway into said motor assembly.

8. The surgical device of claim 7 wherein said handpiece has a housing and further comprising a seal between said static seal element and said housing to prevent said fluid from flowing past said motor assembly.

9. The surgical device of claim 8 wherein said seal comprises at least one resilient O-ring.

10. A surgical device for operating a rotatable surgical tool, said surgical device comprising:
a handpiece adapted to receive said surgical tool;
a drive shaft for engaging said surgical tool;
a motor assembly for rotating said drive shaft about an axis;
a static seal element sealed to said motor assembly;
a dynamic seal element sealed to said drive shaft;
a plurality of springs disposed circumferentially about said axis to bias said dynamic seal element axially against said static seal element; and
said static seal element and said dynamic seal element having mating sealing portions defining a face seal in a surface transverse to said axis of rotation of said drive shaft.

11. The surgical device of claim 10 wherein said springs are parallel to said drive shaft.

12. The surgical device of claim 10 further comprising a buffer ring disposed around said drive shaft between said springs and said dynamic seal element.

13. A surgical device for operating a rotatable surgical tool, said surgical device comprising:
a handpiece adapted to receive said surgical tool;
a drive shaft for engaging said surgical tool;
a motor assembly for rotating said drive shaft about an axis;
a static seal element sealed to said motor assembly;
a dynamic seal element sealed to said drive shaft;
said static seal element and said dynamic seal element having mating sealing portions defining a face seal in a surface transverse to said axis of rotation of said drive shaft; and
said static seal element and said dynamic seal element being rings, the outer diameter of said static seal element being greater than the outer diameter of said dynamic seal element, said dynamic seal element defining an inward step which reduces the outer diameter of said dynamic seal element at said mating portions.

14. A surgical device for operating a rotatable surgical tool, said surgical device comprising:
a handpiece adapted to receive said surgical tool;
a drive shaft for engaging said surgical tool;
a motor assembly for rotating said drive shaft about an axis;
a static seal element sealed to said motor assembly;
a dynamic seal element sealed to said drive shaft; and
said static seal element and said dynamic seal element having mating sealing portions defining a face seal in a surface transverse to said axis of rotation of said drive shaft, the mating portions of said static seal element and said dynamic seal element being lapped flat to within 3 helium light bands.

15. A surgical device for operating a rotatable surgical tool, said surgical device comprising:
a handpiece adapted to receive said surgical tool;
a drive shaft for engaging said surgical tool, a portion of said drive shaft defining a groove;
a motor assembly for rotating said drive shaft about an axis;
a static seal element sealed to said motor assembly;
a dynamic seal element sealed to said drive shaft,
a ring seal positioned within said groove to seal said drive shaft to said dynamic seal element; and
said static seal element and said dynamic seal element having mating sealing portions defining a face seal in a surface transverse to said axis of rotation of said drive shaft.

16. The surgical device of claim 15 wherein said ring seal maintains distance between said drive shaft and said dynamic seal element.

17. A surgical device for operating a rotatable surgical tool, said surgical device comprising:
a handpiece adapted to receive said surgical tool;
a drive shaft for engaging said surgical tool;
a motor assembly for rotating said drive shaft about an axis;
a static seal element sealed to said motor assembly;
a dynamic seal element sealed to said drive shaft and coupled to said drive shaft through a member that is axially slidable along said drive shaft and keyed to be rotatably fixed relative to said drive shaft and said dynamic seal element; and said static seal element and said dynamic seal element having mating sealing portions defining a face seal in a surface transverse to said axis of rotation of said drive shaft.

18. The surgical device of claim 17 further comprising a plurality of springs which bias said member toward said dynamic seal element to in turn press said dynamic seal element toward said static seal element.

19. The surgical device of claim 18 further comprising a buffer ring disposed around said drive shaft between said member and said dynamic seal element, said buffer ring acting as a resilient interface between said member and said dynamic seal element.

* * * * *

(12) REEXAMINATION CERTIFICATE (4730th)
United States Patent
Sjostrom

(10) Number: US 5,133,729 C1
(45) Certificate Issued: Feb. 11, 2003

(54) MOTOR DRIVEN HAND PIECE FOR A SURGICAL TOOL

(75) Inventor: Douglas D. Sjostrom, Wakefield, MA (US)

(73) Assignee: Smith & Nephew, Inc., Andover, MA (US)

Reexamination Request:
No. 90/003,782, Apr. 6, 1995

Reexamination Certificate for:
Patent No.: 5,133,729
Issued: Jul. 28, 1992
Appl. No.: 07/569,082
Filed: Aug. 17, 1990

(51) Int. Cl.[7] .............................................. A61B 17/32
(52) U.S. Cl. .......................... 606/180; 604/22; 408/124
(58) Field of Search .......................... 604/22; 606/167, 606/168, 170, 171, 180; 408/124, 127, 199, 226

(56) References Cited

U.S. PATENT DOCUMENTS

| | | |
|---|---|---|
| 3,409,213 A | 11/1968 | Latham, Jr. |
| 3,638,957 A | 2/1972 | Marsi |
| 3,957,276 A | 5/1976 | Wiese |
| 3,990,453 A | 11/1976 | Douvas et al. |
| 4,026,564 A | 5/1977 | Metcalfe |
| 4,167,943 A | 9/1979 | Banko |
| 4,167,944 A | 9/1979 | Banko |
| 4,203,444 A | 5/1980 | Bonnell et al. |
| 4,246,902 A | 1/1981 | Martinez |
| 4,274,414 A | 6/1981 | Johnson et al. |
| 4,517,977 A | 5/1985 | Frost |
| 4,545,588 A | 10/1985 | Nagai et al. |
| 4,625,712 A | 12/1986 | Wampler |
| 4,802,458 A | 2/1989 | Finsterwald et al. |
| 5,112,299 A * | 5/1992 | Pascaloff ..................... 604/22 |
| 5,118,264 A | 6/1992 | Smith |

FOREIGN PATENT DOCUMENTS

| | | |
|---|---|---|
| JP | 4729739 | 11/1972 |
| JP | 6346538 | 12/1988 |

OTHER PUBLICATIONS

Baumeister et al, Standard Handbook for Mechanical Engineers, pp. 8–188 to 8–193, 1958.
Shigley et al, Standard Handbook of Machine Design, pp. 26.2 to 26.39, 1986.

* cited by examiner

Primary Examiner—Sharon Kennedy

(57) ABSTRACT

A surgical device including a handpiece adapted to receive a surgical tool, a motor driven drive shaft for rotating the tool about an axis, a static seal element sealed to the motor assembly, and a dynamic seal element sealed to the drive shaft, the seal elements having mating sealing portions defining a face seal in a surface transverse to the axis of rotation of the drive shaft.

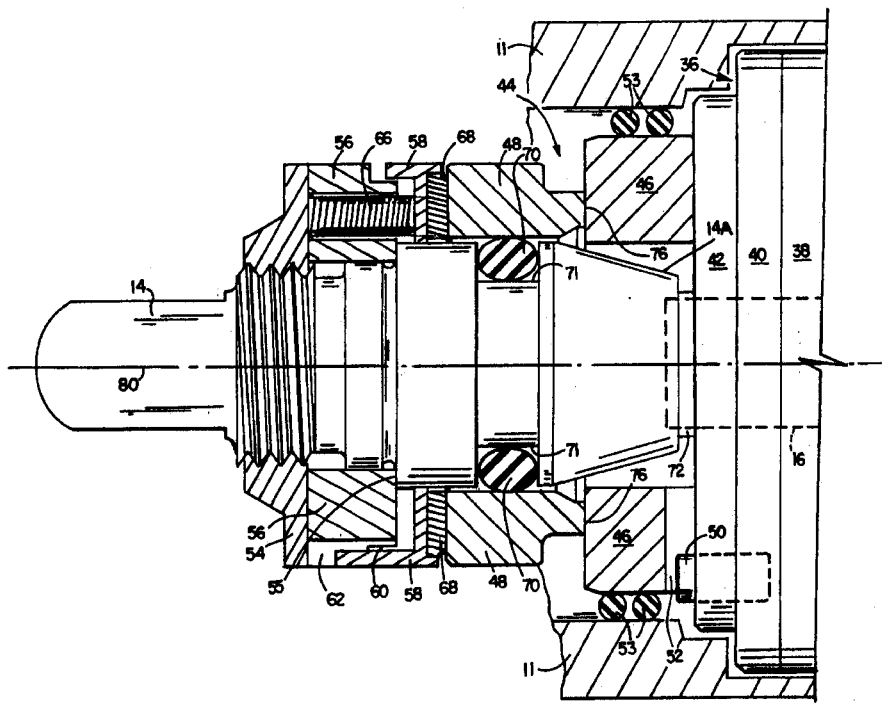

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 10–19 is confirmed.

Claims 1–9 are cancelled.

\* \* \* \* \*